United States Patent [19]

Gaboury et al.

[11] Patent Number: 5,556,992
[45] Date of Patent: Sep. 17, 1996

[54] NOVEL RHODAMINE DERIVATIVES FOR PHOTODYNAMIC THERAPY OF CANCER AND IN VITRO PURGING OF THE LEUKEMIAS

[75] Inventors: Louis Gaboury; Luc Villeneuve; Richard Giasson; Tiechao Li, all of Montréal; Ajay K. Gupta, Pointe-Claire, all of Canada

[73] Assignee: Universite de Montreal, Montreal, Canada

[21] Appl. No.: 300,179

[22] Filed: Sep. 2, 1994

[51] Int. Cl.[6] .................................................. C07D 311/82
[52] U.S. Cl. .................................................. 549/227
[58] Field of Search ................................................ 549/227

[56] References Cited

U.S. PATENT DOCUMENTS 4,977,278  12/1990  Schmeidl ................................ 549/227

OTHER PUBLICATIONS

Vora et al., J. Labelled Compd. Radiopharm., 28(1), 1–14 (1990).

*Primary Examiner*—Nicky Chan
*Attorney, Agent, or Firm*—Klauber & Jackson

[57] ABSTRACT

The present invention relates to novel photoactivable rhodamine derivatives for enhancing high quantum-yield production and singlet oxygen generation upon irradiation with light while maintaining desirable differential retention of rhodamine between normal and cancer cells, said derivatives are selected from the group consisting of 4,5-dibromorhodamine 123 (2-(4,5-dibromo-6-amino-3-imino-3H-xanthen-9-yl)-benzoic acid methyl ester hydrochloride); 4,5-dibromorhodamine 123 (2-(4,5-dibromo-6-amino-3-imino-3H-xanthen-9-yl)-benzoic acid ethyl ester hydrochloride); 4,5-dibromorhodamine 123 (2-(4,5-dibromo-6-amino-3-imino-3H-xanthen-9-yl)-benzoic acid octhyl ester hydrochloride); 4,5-dibromorhodamine 110 n-butyl ester (2-(4,5-dibromo-6-amino-3-imino-3H-xanthen-9-yl)-benzoic acid n-butyl ester hydrochloride); Rhodamine B n-butyl ester (2-(6-ethyl amino-3-ethyl imino-3H-xanthen-9-yl)-benzoic acid n-butyl ester hydrochloride); and photoactivable derivatives thereof; whereby photoactivation of the derivatives induces cell killing while unactivated derivatives are substantially non-toxic to cells. Also, the present invention relates to the use of the photoactivable derivatives of the present invention for the photodynamic therapy of a cancer patient by destroying human cancer cells, wherein appropriate intracellular levels of the derivatives are achieved and irradiation with light of a suitable wavelength is applied. The present invention also relates to a method for the photodynamic therapy of a patient suffering from leukemias, disseminated multiple myelomas or lymphomas.

1 Claim, 3 Drawing Sheets

NOVEL RHODAMINE DERIVATIVES FOR PHOTODYNAMIC THERAPY OF CANCER AND IN VITRO PURGING OF THE LEUKEMIAS

BACKGROUND OF THE INVENTION (a) Field of the Invention

The invention relates to a photodynamic treatment for the selective destruction of malignant leukemic cells without affecting the normal cells and without causing systemic toxicity for the patient.

(b) Description of Prior Art

Cancers are uncontrolled cell proliferations that result from the accumulation of genetic changes in cells endowed with proliferative potential. After a variable latency period during which they are clinically silent, the malignant cells progress to aggressive invasive and metastatic stages with tumor formation, bleeding, susceptibility to infections, and widespread dissimination throughout the body.

Despite important advances in treatment, cancers still acount for 28% of death in Western countries. Treatment of cancer has relied mainly on surgery, chemotherapy, radiotherapy and more recently immunotherapy. Significant improvement in outcome has occured with the use of combined modalities, for a small number of cancers. However, for the most frequent types of cancers (lung, breast, colo-rectal and the leukemias) complete remission and cure has not been achieved. Therefore, the development of new approaches for treating cancer patients is critically needed particularly for those patients whose disease has progressed to a metastatic stage and are refractory to standard chemotherapy. To overcome resistance, autologous stem cell transplantation (AuSCT) has been employed in the treatment of a number of advanced forms of cancer. Because high-dose chemotherapy with or without total body irradiation can be applied prior to AuSCt, increased response rates have been observed when compared with standard chemotherapy. One important issue that needs to be stressed when using AuSCT relates to the risk of reinfusing residual tumor cells despite histologic remission. A variety of techniques have been developed that can deplete up to $10^5$ of tumor cells from the marrow. These techniques, including immunologic and pharmacologic purging, are not entirely satisfactory. One major consideration when purging bone marrows is to preserve the normal hemopoietic stem cell compartment so that normal hemopoiesis can rapidly become reestablished upon grafting. The potential of photodynamic therapy, in association with photosensitizing molecules capable of destroying malignant cells while sparing normal hemopoietic stem cells, to purge bone marrow in preparation for AuSCT has largely been unexplored. This issue has been investigated in depth for one type of neoplasm, chronic myeloid leukemia (CML), since AuSCT has the potential to cure the disease and highly sensitive molecular biologic techniques are currently available to determine the efficacy of the purging procedure. Application of photodynamic therapy for treating other forms of leukemias, lymphomas and metastatic solid tumors is a distinct possibility in view of the functionnal properties of the dyes molecules which were synthesized in accordance with the present invention and whose description appears below.

Chronic myeloid leukemia (CML) comprises 15% of the leukemias. It is a clonal pluripotent hemopoietic stem cell disorder characterized by deregulated proliferation of bone marrow progenitors and circulating terminally differentiated myeloid cells. If left untreated this disease is invariably fatal.

Genetic analysis on CML cells has identified a highly characteristic abnormality consisting of a balanced translocation involving chromosome 9 and 22 where part of the c-abl protooncogene on chromosome 9 is juxtaposed to the 5' end of the bcr-1 gene on chromosome 22, leading to the formation of a fusion gene, a chimeric transcript and a P210 bcr/abl protein with tyrosine kinase activity. CML cells harboring the translocation are known as Ph-1+ cells, whereas non-clonal, presumably normal but suppressed marrow cells are known as Ph-1 negative (Ph-1-) cells.

Treatment of CML patient aims at eradicating Ph-1+ cells and reestablishing non-clonal Ph-1-hemopoiesis. Conventional myelosuppressive therapy with hydroxyurea, busulfan, and more recently with interferon-alpha (IFN-alpha) and hemoharringtonine (HTT) have failed to provide prolonged or complete clinical and cytogenetic remissions (reviewed in Goldman J. M. (1994) *Blood Reviews*, 8: 21–29). To date only allogenic bone marrow transplantation (ABMT) in young patients (<55 years) with human leukocyte antigen-compatible (HLA-compatible) sibblings donor marrow has been shown to be curative in over 50% of good risks patients. However, only a minority of patients (20%) is eligible for allogenic bone marrow transplantation because of the lack of suitably matched donors or because patients are deemed too old to withstand the procedure. Therefore, alternative strategies to treat CML had to be developed. One promising line of research that has produced exciting results consists of restoring Ph- hemopoiesis by grafting patient's own marrow or peripheral blood stem cells that were harvested in chronic phase prior to intensive chemotherapy and total body irradiation. This procedure, known as autologous stem cell transplantation (AuSCT) involves, no or some ex vivo marrow manipulations to purge residual malignant Ph+ leukemic cells. To achieve eradication of the Ph-1+ clone several approaches have been proposed including:

1) in vitro exposure of the graft to 4-perhydroxycyclophosphamide (4-HC) or to a more stable derivative Mafosfamide™ (Asta-Z 7557);

2) in vitro selection by growth in long-term culture;

3) positive selection of CD34+DR- non-clonal stem cells; and 4) in vivo therapy with combinations of antileukemic agents or with interferon-alpha followed by transplant.

However, the clinical relevance of these methods remains to be established.

There are many reports on the use of photodynamic therapy in the treatment of malignancies (Daniell M. D., Hill J. S. (1991) *Aust. N. Z. J. Surg.*, 61: 340–348). The method has been applied for cancers of various origins and more recently for the eradication of viruses and pathogens (Raab O. (1900) *Infusoria Z. Biol.*, 39: 524).

The initial experiments on the use photodynamic therapy for cancer treatment using various naturally occuring or synthetically produced photoactivable substances were published early this century (Jesionek A., Tappeiner V. H. (1903) *Muench Med Wochneshr*, 47: 2042; Hausman W. (1911) *Biochem. Z.*, 30: 276). In the 40's and 60's, a variety of tumor types were subjected to photodynamic therapy both in vitro and in vivo (Kessel, David (1990) *Photodynamic Therapy of neoplastic disease*, Vol. I, II, CRC Press. David Kessel, Ed. ISBN 0-8493-5816-7 (v. 1), ISBN 0-8493-5817-5 (v. 2)). Dougherty et al. and others, in the 70's and 80's, systematically explored the potential of oncologic application of photodynamic therapy (Dougherty T. J.

(1974) *J. Natl Cancer Inst.*, 51: 1333–1336; Dougherty T. J. et al. (1975) *J. Natl Cancer Inst.*, 55: 115–121; Dougherty T. J. et al. (1978) *Cancer Res.*, 38: 2628–2635; Dougherty T. J. (1984) *Urol. Suppl.*, 23: 61; Dougherty T. J. (1987) *Photochem. Photobiol.*, 45: 874–889).

Treatment of leukemia with photodynamic therapy

There is currently a lack of antineoplastic agents which allow selective destruction of expanded leukemic cells while leaving intact the normal but suppressed residual cellular population. Preferential uptake of photosensitive dye and cytotoxicity of photodynamic therapy against leukemia cells have been previously demonstrated (Jamieson C. H. et al. (1990) *Leuk. Res.*, 14: 209–219).

It would be highly desirable to be provided with new photosensitizers which possess the following characteristics:

i) preferential localization and uptake by the malignant cells;

ii) upon application of appropriate light intensities, killing those cells which have accumulated and retained the photosensiting agents;

iii) sparing of the normal hemopoietic stem cell compartment from the destructive effects of activated photosensitizers; and iv) potential utilization of photosensitizers for bone marrow purging of harvested marrow in preparation for autologous bone marrow transplantation.

The Rhodamine dyes

Rhodamine 123 (2-(6-amino-3-imino-3H-xanthen-9-yl) benzoic acid methyl ester hydrochloride), a lipophilic cationic dye of the pyrylium class which can disrupt cellular homeostasis and be cytostatic or cytotoxic upon high concentration exposure and/or photodynamic therapy, although with a very poor quantum yield (Darzynkiewicz Z., Carter S. (1988) *Cancer Res.*, 48: 1295–1299). It has been used in vitro as a specific fluorescent stain for living mitochondria. It is taken up and is preferentially retained by many tumor cell types, impairing their proliferation and survival by altering membrane and mitochondrial function (Oseroff A. R. (1992) In *Photodynamic therapy* (Henderson B. W., Dougherty T. J., eds) New York: Marcel Dekker, pp. 79–91). In vivo, chemotherapy with rhodamine 123 can prolong the survival of cancerous mice, but, despite initial attemps to utilize rhodamine 123 in the treatment of tumors, its systemic toxicity of rhodamine 123 may limit its usefulness (Bernal, S. D., et al. (1983) *Science*, 222: 169; Powers, S. K. et al. (1987) *J. Neurosur.*, 67: 889).

U.S. Pat. No. 4,612,007 issued on Sep. 16, 1986 in the name of Richard L. Edelson, discloses a method for externally treating human blood, with the objective of reducing the functioning lymphocyte population in the blood system of a human subject. The blood, withdrawn from the subject, is passed through an ultraviolet radiation field in the presence of a dissolved photoactive agent capable of forming photoadducts with lymphocytic-DNA. This method presents the following disadvantages and deficiencies. The procedure described is based on the utilization of known commercially available photoactive chemical agents for externally treating patient's blood, leaving the bone marrow and potential resident leukemic clones intact in the process. According to Richard L. Edelson, the method only reduces, does not eradicate, the target cell population. Moreover, the wavelength range of UV radiation used in the process proposed by Richard L. Edelson could be damageable to the normal cells.

International Application published on Jan. 7, 1993 under International publication number WO 93/00005, discloses a method for inactivating pathogens in a body fluid while minimizing the adverse effects caused by the photosensitive agents. This method essentially consists of treating the cells in the presence of a photoactive agent under conditions that effect the destruction of the pathogen, and of preventing the treated cells from contacting additional extracellular protein for a predetermined period of time. This method is concerned with the eradication of infectious agents from collected blood and its components, prior to storage or transfusion, and does not impede on the present invention.

It would be highly desirable to be provided with a new approach for the use of rhodamine derivatives in the treatment of tumors which overcomes these drawbacks while having no systemic toxicity for the patient.

SUMMARY OF THE INVENTION

Since autologous stem cell transplantation (AuSCT) offers a potentially curative strategy if normal hematopoietic cells could be separated from neoplastic stem cells either in vitro or in vivo, the possibility was investigated, of using photosensitizing dyes with high quantum efficiencies of phototoxic activity in combination with photodynamic therapy (PDT) to achieve selective eradication of the Ph-1+ leukemic cells. In sharp contrast with isolated reports describing PDT-based purging of marrow using merocyanine-sensitized photoinactivation, the molecules of the present invention were designed to take advantage of the known exclusion of rhodamine-123 and its derivatives (personal observations) from normal hemopoietic stem cells which stain poorly with rhodamine 123 and yet maintain extensive self-renewal in vitro. Moreover, because PDT-based bone marrow purging does not preclude the use of other means of effecting positive and/or negative selection of marrows it could be used in conjunction with other therapeutic regimens.

One aim of the present invention is to produce new photosensitizers endowed with the following characteristics:

i) preferential localization and uptake by the malignant cells;

ii) upon application of appropriate light intensities, killing those cells which have accumulated and retained the photosensitizing agents;

iii) sparing of the normal hemopoietic stem cell compartment from the destructive effects of activated photosensitizers; and iv) potential utilization of photosensitizers for bone marrow purging of harvested marrow in preparation for autologous bone marrow transplantation.

Accordingly, the method of the present invention using photodynamic therapy was structured so as to eradicate the malignant clonogenic cells from CML bone marrow.

Another aim of the present invention is to provide, using rhodamine derivatives, a new method for the treatment of tumors which overcomes the systemic toxicity problems, inasmuch as photodynamic therapy is used in vitro for the purging of cancerous clones from the bone marrow of chronic myelogenous leukemia (CML) patients.

In accordance with the present invention, the phototoxicity of rhodamine B n-butylester (2-(6-ethyl amino-3-ethyl imino-3H-xanthen-9-yl) benzoic acid n-butyl ester hydrochloride), 4,5-dibromorhodamine 110 n-butyl ester (2-(4,5- dibromo-6-amino-3-imino-3H-xanthen-9-yl) benzoic acid n-butyl ester hydrochloride) and 4,5-dibromorhodamine 110 n-butyl ester (2-(4,5-dibromo-6-amino-3-imino-3H-xanthen-9-yl) benzoic acid methyl ester hydrochloride) and other esters (ethyl, octyl) have been assessed.

In accordance with the present invention, there is provided photoactivable rhodamine derivatives for enhancing high quantum-yield production and singlet oxygen generation upon irradiation while maintaining desirable differential retention of rhodamine between normal and cancer cells, said derivatives are selected from the group consisting of 4,5-dibromorhodamine 123 (2-(4,5-dibromo-6-amino-3-imino-3H-xanthen-9-yl)-benzoic acid methyl ester hydrochloride); 4,5-dibromorhodamine 123 (2-(4,5-dibromo-6-amino-3-imino-3H-xanthen-9-yl)-benzoic acid ethyl ester hydrochloride); 4,5-dibromorhodamine 123 (2-(4,5-dibromo-6-amino-3-imino-3H-xanthen-9-yl)-benzoic acid octhyl ester hydrochloride); 4,5-dibromorhodamine 110 n-butyl ester (2-(4,5-dibromo-6-amino-3-imino-3H-xanthen-9-yl)-benzoic acid n-butyl ester hydrochloride); Rhodamine B n-butyl ester (2-(6-ethyl amino-3-ethyl imino-3H-xanthen-9-yl)-benzoic acid n-butyl ester hydrochloride); and photoactivable derivatives thereof; whereby photoactivation of said derivatives induces cell killing while unactivated derivatives are substantially non-toxic to cells.

In accordance with the present invention, the complete growth inhibition of tumor cell lines is achieved in vitro after photodynamic therapy effected with the above-mentioned photosensitizers. This effect contrasts with the lack of inhibitory effect upon exposure to either light alone or to a saturating concentration of the photosensitizers.

Due to the specific retention of the rhodamine 123 class of dyes by the abnormal malignant cells and the concomitant lack of their accumulation by the normal hematopoietic stem cells, these results provide evidence for the potential use of these three new dyes for in vivo or in vitro photodynamic therapy.

DETAILED DESCRIPTION OF THE INVENTION

Figure 1:
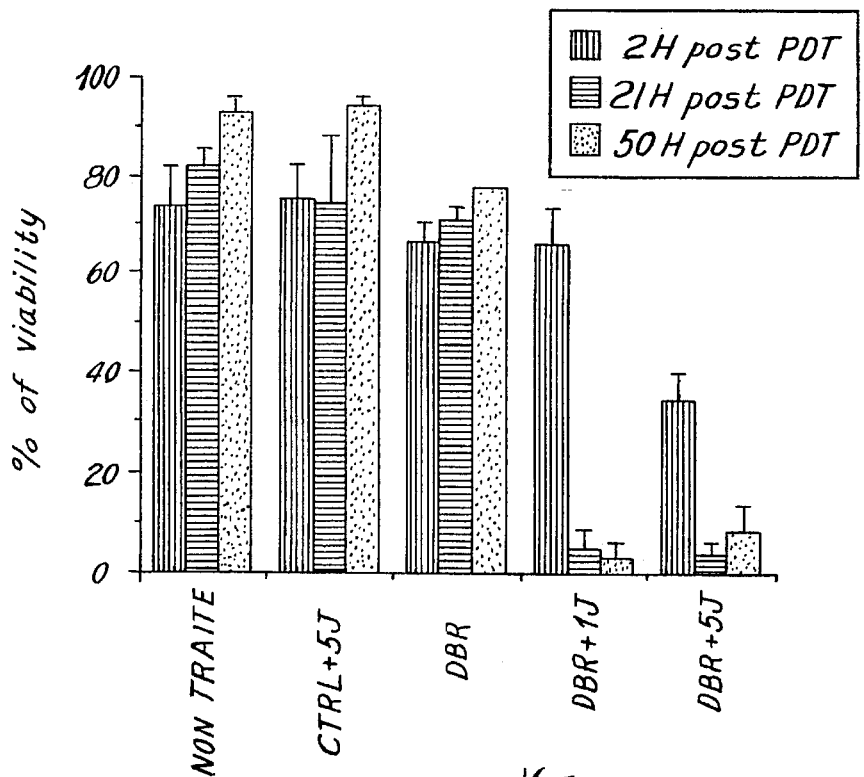
FIG. 1 is a graph of the photo toxicity of 4,5-dibromorhodamine 123 used in accordance with the method of the present invention and expressed in % viability.

Photoactive dyes are excited from the ground state to the singlet excited state following absorption of photons. Singlet excited states of organic molecules generally have short lifetimes ($10^{-12}$–$10^{-6}$ sec.) as they rapidly relax back to the ground state using, non-radiative (vibrational modes) and radiative (fluorescence) processes. Intersystem crossing to the more stable triplet excited state is also competing with relaxation to the ground state. Triplet excited states generally have longer lifetimes (10–6–10 sec) which allow them to diffuse and react with other molecules in the medium.

Reactivity between molecular oxygen and a photosensitizer excited to the triplet state, both present in malignant cells, is the operating principle of most photodynamic therapies. Triplet excited states can react with molecular oxygen via two different mechanisms. The first mechanism (Type I) consists of the transfer of an electron from the excited dyes to molecular oxygen, resulting in highly reactive free radicals being present in the cellular environment.

The second mechanism (Type II) consists of the transfer of energy from the excited dyes to molecular oxygen, leading to the formation of cytotoxic singlet oxygen.

Photosensitizers must therefore meet two conditions in order to be an effective phototherapeutic agent. The first condition is that they must be present at a far higher concentration in malignant cells than that in normal cells. A higher concentration of dyes in malignant cells results in a higher concentration of photogenerated cytotoxic species and therefore in a higher death rate. The second condition is that irradiation of the phototherapeutic agent, in the presence of intracellular concentrations of molecular oxygen, must lead to the formation of the cytotoxic species with high efficiency.

Rhodamine 123 is known to be taken up and preferentially retained by many tumor cells and consequently its use as a phototherapeutic agent has been proposed. However, the singlet excited state of Rhodamine 123 does not undergo intersystem crossing to the triplet excited state efficiently. Because of this, Rhodamine 123 is a weak phototoxin (Morliere, P et al. (1990) *Photochemistry and Photobiology*, 52(4): 703–710).

To overcome the limitations of the prior art methods, the chemical structure of rhodamine 123 can be modified in such a way as to enhance intersystem crossing to the triplet excited state. Theoretically, this could be achieved by substituting heavy atoms, such as Br or other halides, for hydrogen atoms in the molecular structure of rhodamine 123. Therefore, dibromorhodamine 123 has been prepared and tested.

The amphiphatic structure and hydrophilicity of the dyes could modulate the cytoplasmic and mitochondrial membranes and affect the phototoxicity of the dye. For example, hydrophobicity was shown to be the most important factor influencing the in vitro uptake of porphyrins (Chi-Wei Lin (1990) In *Photodynamic therapy of neoplastic disease*, Vol II, CRC Press, pp 79–101). Therefore, different esters of rhodamine 123 and rhodamine B were prepared and tested. More specifically dibromorhodamine n-butyl ester (DBBE) and rhodamine B n-butyl-ester (RBBE).

Different heavy atom substitutions of the hydrogen atoms (halogenic substitution) of the rhodamine backbone, for example, dibromo and diiodo derivatives of rhodamine B and Rh 110, are being prepared and tested.

Dimers/oligomers, hetero dimers/oligomers of such compounds also will be prepared and tested.

Substitution of the oxygen heteroatom of the rhodamine backbone by a heavier atom to reduce $S_0/S_1$ splitting, theoritically should increase spin orbit coupling and promote intersystem crossing from the $S_1$ to the $T_1$ state, producing higher triplets yields than the original dye. This should increase proportionally the production of singlet oxygen. Therefore, S (Sulfur), Se (Selenium) and Te (Tellurium) substitutions for the oxygen atom (O) of the rhodamine backbone is explored. More over, other strategies for increasing high quantum yields of Type I (free radicals) or Type II (superoxyde anion or singlet oxygen) products and tumor selective accumulation of the dye are tested.

In accordance with the present invention, there is provided the use of such above-mentioned dyes in conjugation with tumor specific antibodies, or poisonous substances, or liposomal or lipoproteins, or fluorochrome adducts.

In addition, the photosensitizers to be described have the potential to act synergistically in conjunction with other photoactive substances.

Moreover, the negative selection procedure provided by the use of photodynamic treatment does not preclude the use of other means for enriching hematopoietic stem cells such as positive selection with anti-CD34 monoclonal antibodies.

Other Clinical applications

In addition to using photosensitizers in the context of in vitro bone marrow purging for the leukemias and metastatic cancers, the molecules can also be used in vivo for tumor sites directly accessible to exposure to a light source and to appropriate local concentrations of the drugs to be described.

Chemical Synthesis

All flash chromatography was done according to the method of Still et al. (Still W. C. et al. (1978) *J. Org. Chem.*, 43: 2923). Thin-layer chromatography was conducted on silica Gel 60™ (HF-245, E. Merck) at a thickness of 0.20 mm. Nuclear magnetic resonnance spectra were obtained with a Varian VXR 300™ (300 MHz) instrument. Spectral data are reported in the following order: chemical shift (ppm), multiplicity, coupling constants, number of proton, assignment. Low resolution mass spectra using fast atom bombardment (FAB), were obtained on a Kratos MS-50 TA™ spectrometer. Ultraviolet spectra were obtained on a Varian DMS100™ spectrophotometer and data are presented as $\lambda_{max}$.

1. Preparation of rhodamine B n-butylester

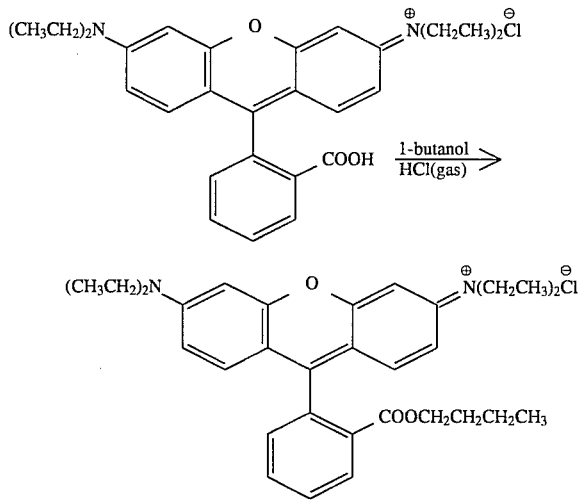

Rhodamine B hydrochloride (150 mg, 0.31 mmol) was dissolved in 1-butanol (5 ml). The reaction mixture was saturated with HCl (gas) and then stirred at 100° C. for 15 hr. 1-Butanol was evaporated under reduced pressure. The crude oily residue was purified by flash chromatography using $CH_2Cl_2$ (200 ml) and then $CH_2Cl_2/CH_3OH$ (85:15) as eluant yielding 142 mg (0.27 mmol, 87% yield) of a dark red solid.

$^1$H NMR (Varian 300 MHz, Acetone, TMS) d 8.31 (dd, J=1.4 and 7.8 Hz, 1H); 7.86–7.94 (M, 2 HO); 7.54 (dd, J=1.5 and 7.4 Hz, 1H); 7.14–7.23 (M, 4H); 7.02 (d, J=2.2 Hz, 2H); 3.97 (t, J=6.3 Hz, 2H); 3.79 (q, J=7.1 Hz, 8H); 1.32 (t, J=7.1 Hz, 12H); 1.2–1.4 (M, 2H); 1.01 (h, J=7.5 Hz, 2H); 0.75 (h, J=7.3 Hz, 3H).

UV (methanol)/$_{max}$:545 nm

2. Preparation of dibromorhodamine n-butylester

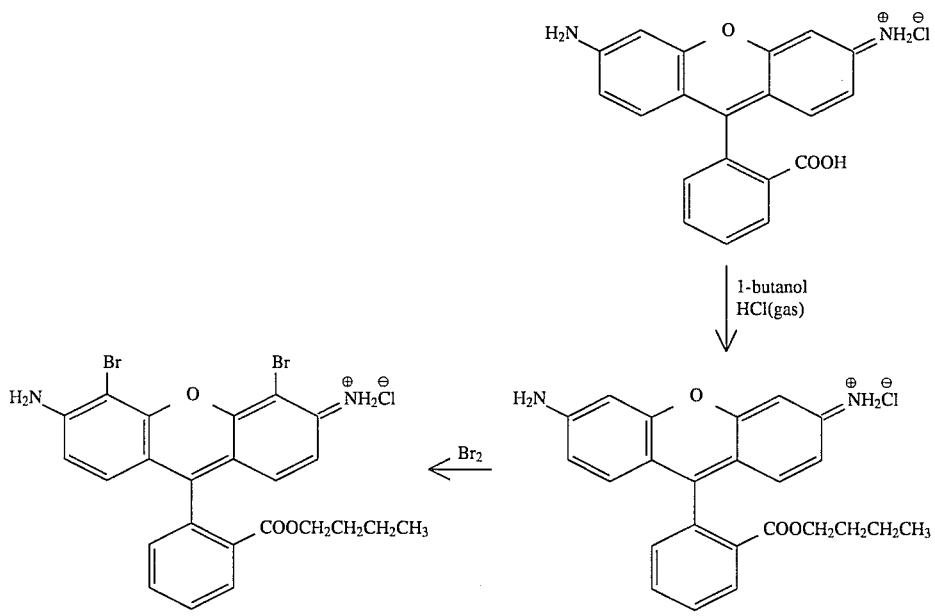

2.1 Preparation of rhodamine n-butylester

Rhodamine 110 (14 mg, 0.038 mmol) was dissolved in 1-Butanol (5 ml). The reaction mixture was saturated with HCl (gas) and then stirred at 100° C. for 15 hr. The 1-Butanol was evaporated under reduced pressure. The crude oily residue was purified by flash chromatography using $CH_2Cl_2/CH_3OH$ (85:15) as eluant yielding 14 mg (0.033 mmol, 87% yield) of a red solid.

2.2 Preparation of dibromorhodamine n-butylester

Rhodamine n-butylester (14 mg, 0.033 mmol) was dissolved in absolute ethanol (3 ml), then bromine (0.0036 ml, 0.070 mmol) was added. The mixture was stirred at room temperature for 1 hr. The solvent was evaporated and the crude reaction residue was purified by flash chromatography using $CH_2Cl_2/CH_3OH$ (85:15) as eluant yielding 15.9 mg (0.027 Mol, 83% yield) of a red solid.

$^1$H NMR (Varian 300 MHz, $CD_3OD$) d 8.31 (dd, J=1.7 and 7.5 Hz, 1H); 7.84 (M, 2H); 7.46 (dd, J=1.8 and 6.9 Hz, 1H); 7.12 (d, J=9.2 Hz, 2H); 7.03 (d, J=9.2 Hz, 2H); 3.95 (t, J=6.2 Hz, 2H); 1.22 (M, 2H); 0.93 (M, 2H); 0.75 (t, J=7.3 Hz, 3H).

MS (LR, FAB) m/z: Calculated for $C_{24}, H_{21}N_2O_3Br_2$; 543 Observed: 543

3. Preparation of dibromorhodamine 123

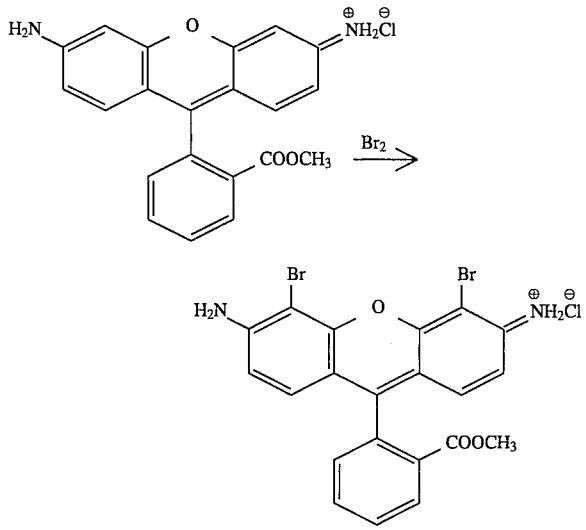

To a solution of rhodamine 123 (25 mg, 0.066 mmol) in dry ethanol (1 ml), was added bromine (0.01 ml, 0.19 mmol) and the resulting mixture was stirred at room temperature for 0.5 hr. Evaporation of solvent in vacuum provided the crude compound which was purified by flash chromatography using $CH_2Cl_2/CH_3OH$ (85:15) as eluant yielding 27.0 mg (0.050 Mol, 77% yield) of a red solid.

$^1$H NMR (Varian 300 MHz, $CD_3OD$) d 8.34 (dd, J=1.7 and 7.5 Hz, 1H); 7.85 (M, 2H); 7.46 (dd, J=1.7 and 7.2 Hz, 1H); 7.10 (d, J=9.2 Hz, 2H); 7.01 (d, J=9.2 Hz, 2H); 3.64 (s, 3H); 8.3 (d, 1H, 9.1 Hz, aromatic), 7.9 (m, 2H, aromatic), 7.45 (d, 1H, 9.1 Hz, aromatic), 7.0, 7.2 (AB system, 4H, aromatic), 3.64 (s, 3H, $OCH_3$).

MS (LR, FAB) m/z: Calculated for $C_{24}, H_{21}N_2O_3Br_2$; 501 Observed: 501

UV (methanol)/$_{max}$: 510 nm

Physical and photochemical properties

After synthesis, the purity of the preparation of the dyes was assessed by NMR analysis and was shown to be over 95%. Absorption and emission spectra were determined for each dye.

Evaluation of cell viability

The K562 chronic myelogeneous leukemia cell line (Lozzio, B. B. and Lozzio, C. B. (1979) *Cancer Res.*, 3(6): 363–370) was obtained from the American Type Culture Collection (ATCC, 12301 Parklawn Drive, Rockville, Md. 20852 USA) under the accession number F-10601 R243-CCL. Cultures were maintained at 37° C. in a humidified incubator with an atmosphere of 95% air and 5% $CO_2$. The culture media (IMDM (Iscove Modified Dulbeco Media) supplemented with 10% fetal bovine serum) were changed bi-weekly and the cells resuspended at a concentration of 100,000/ml. Cells were shown to be mycoplasma negative by routinely testing at 4 weeks interval.

Before each experiment, cell viability was assessed and $2\times10^6$ viable cells were distributed in each 15 ml test tube. Cells were then incubated for 1 hour at 37° C., spun down and the cell pellet resuspended in the culture media in the presence or absence of dye. The cells were then incubated for the appropriate time at 37° C., generally 40 minutes, then washed twice in PBS (Phosphate Buffer Saline) and resuspended in the culture media. Photodynamic therapy was then applied to the cell culture, immediately or after an incubation period at 37° C. The cell cultures were kept at 4° C. during the application of photodynamic activation.

Phototoxicity of 4,5-dibromorhodamine 123

To assess the photochemotherapeutic potential and the in vitro phototoxicity of 4,5-dibromorhodamine 123 (DBR), the leukemic K-562 cell line assay (as described above) was applieded. Exposure to 514.5 nm radiation from an argon ion laser at 10 $J/cm^2$ induced photo toxicity in K-562 cells treated with DBR at a final concentration of 10 μg/ml. DBR was shown to be markedly more phototoxic than rhodamine 123; the increased activity is believed to be a consequence of increased intersystem crossing of DBR to the triplet manifold via spin orbital-coupling induced by the heavy atoms. As shown in FIG. 1, dibromorhodamine is extremely phototoxic at doses as little as 1 $J/cm^2$ and the cell viability drops under 5% in less than 24 hours after irradiation.

Phototoxicity of 4,5-dibromorhodamine 110 n-butyl ester

Figure 2A:
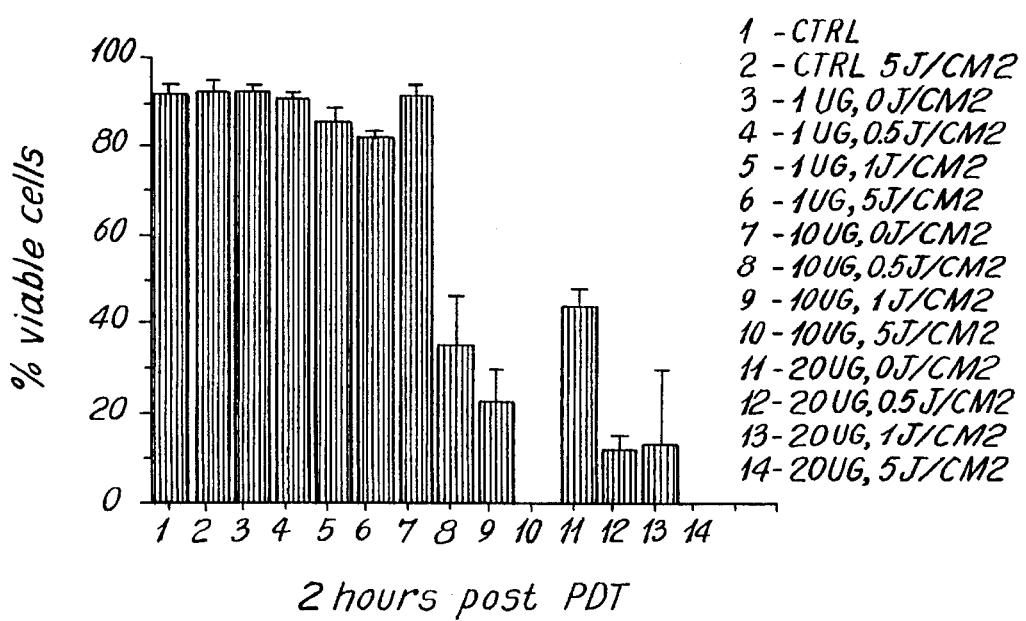
FIG. 2 shows three graphs of the photo toxicity of 4,5-dibromorhodamine 110 n-butyl ester used in accordance with the method of the present invention and expressed in % viability.
Figure 2B:
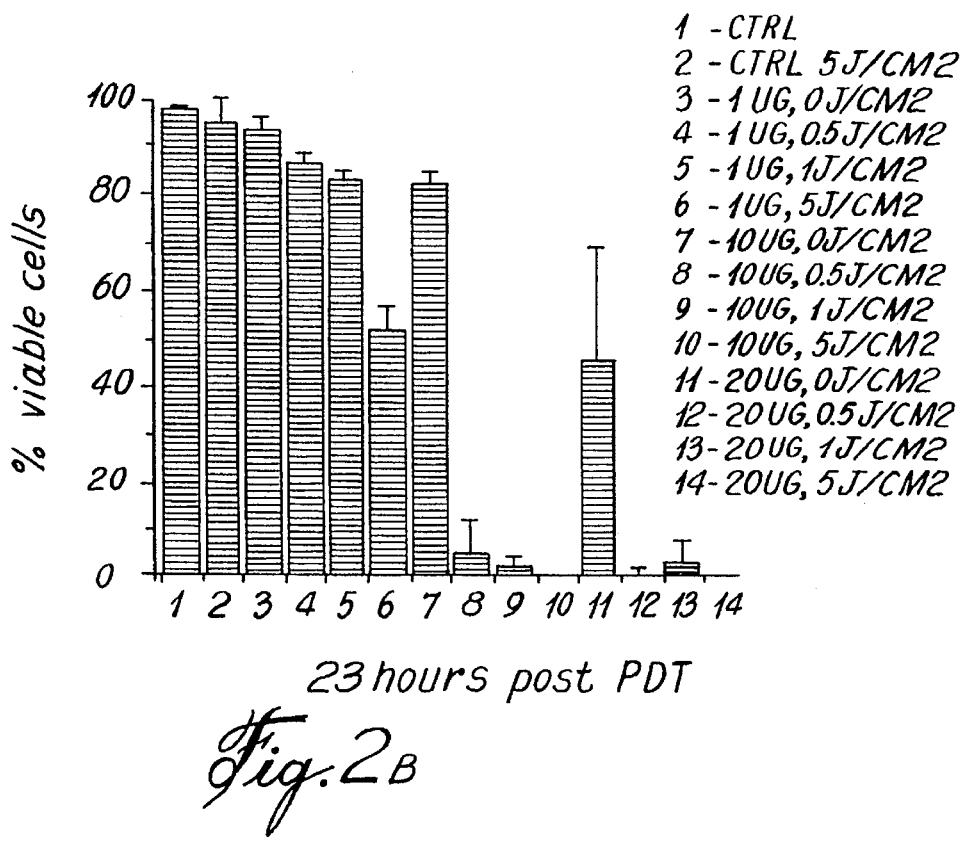
Figure 2C:
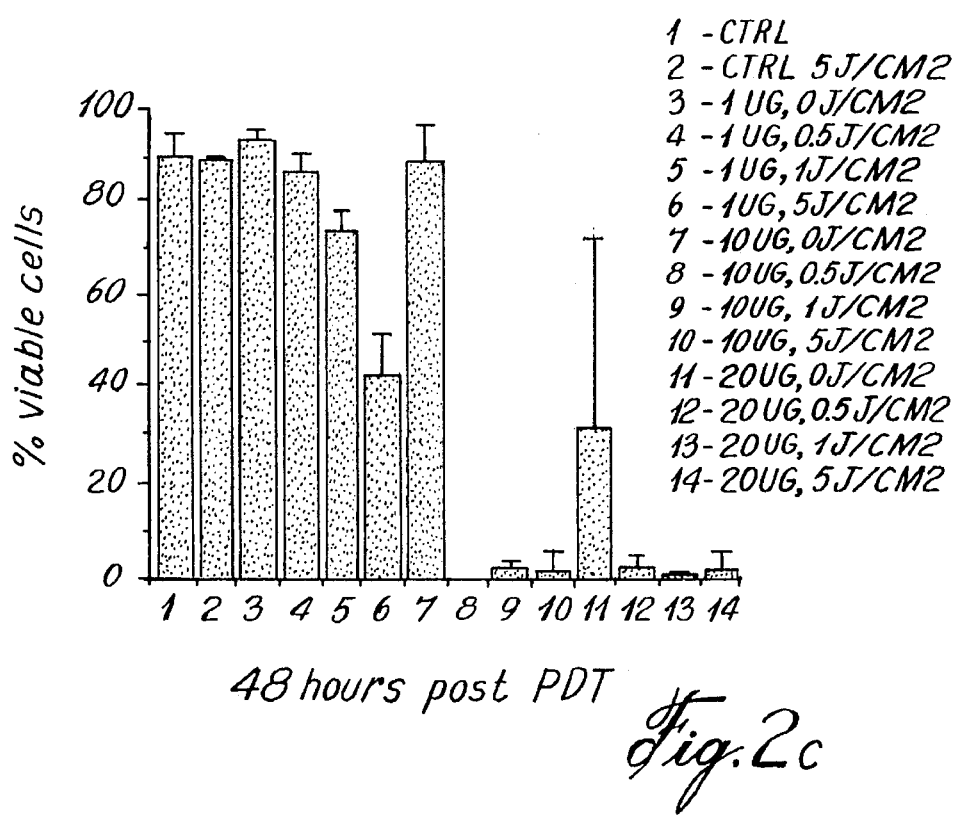

To ascertain the photochemotherapeutic potential of 4,5-dibromorhodamine 110 n-butyl ester (DBBE), in vitro phototoxicity was evaluated in the K-562 cell line procedure described. The cells were incubated with increasing concentrations of DBBE and the cell viability was measured at different time points following photodynamic therapy. The results shown in FIG. 2 show that a dosage of 10 μg/ml of the dye and a brief exposure at 0.5 $J/cm^2$ completely suppress cell viability in less than 24 hours after irradiation.

Photo toxicity of Rhodamine B n-butyl ester

Figure 3A:
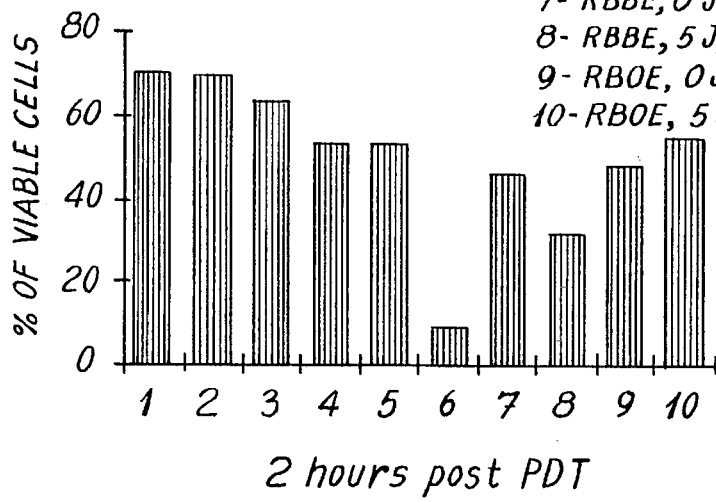
FIG. 3 shows two graphs of the photo toxicity of rhodamine B n-butyl ester used in accordance with the method of the present invention and expressed in % viability.
Figure 3B:
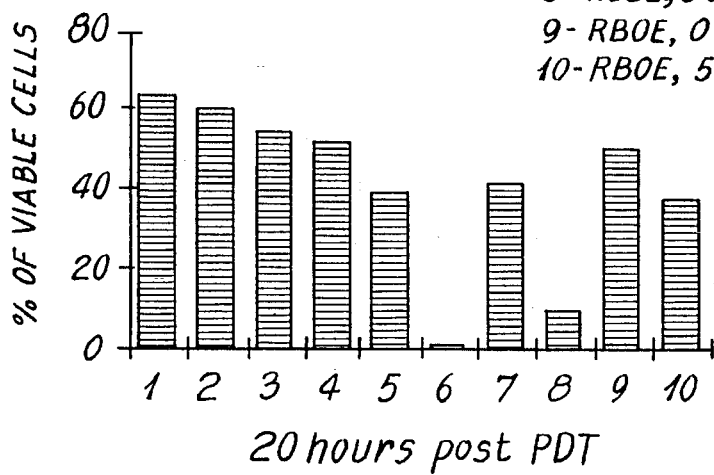

The photo toxicity in vitro of rhodamine B n-butyl ester (RBBE) was evaluated in the K-562 cell line procedure, in order to assess its photochemotherapeutic potential. Comparison was made to the induced phototoxicity of rhodamine 123 (123RH) and of rhodamine B butyl ester. Cell viability was evaluated 2 and 20 hours after photodynamic therapy. The results shown in FIG. 3 demonstrate that a dosage of 10 μg/ml of the dye and a photo exposure of 5 J/cm² significantly suppress cell viability of K562 cells in less than 20 hours after irradiation. Rhodamine 123 has no effect on cell viability, even at exposures of 10 J/cm².

Phototoxicity against bone marrow cultures

It is observed that the photo treatment alone, at energy levels up to 10 J/cm2, or the pre-incubation of the cells at saturating concentrations of the dyes did not affect neither the establishment of the long term culture nor the formation in semi solid assays of cellular colonies issued from the multiplication and differentiation of committed progenitors present in the bone marrow (colony forming units-erythrocytes (CFU-E), blast forming units-erythrocytes (BFU-E), colony forming units-granulocytes, macrophages, (CFU-G-M)). However, as reported for rhodamine 123, the LTC (Long Term Culture) establishment is more sensitive to the dyes but the number of viable commited precursor and stem cells remains unaffected. Photodynamic therapy with rhodamine 123, rhodamine B n-butyl ester and 4,5-dibromorhodamine n-butyl ester minimally impaired the establishment of normal mouse long term culture of bone marrow and the formation of hematopoietic colonies in semi-solid assays. This is in agreement with results obtained previously in other laboratories using rhodamine 123.

Conventional approaches for the treatment of cancer such as radiotherapy and intensive chemotherapy are limited by their intrinsic toxicity and myelosuppressive effects. The introduction of allogeneic and autologous bone marrow transplantation have allowed the administration of marrow ablative chemotherapy and radiotherapy to patients whose malignancies cannot be cured with less aggressive measures. However, allogeneic bone marrow transplantation is not widely accessible to patients because of the lack of suitable donnors and the onset of graft-versus-host disease in recipients. To overcome these limitations and to expand the number of patients and age limit for intensive curative therapy, the potential benefit of in vitro bone marrow purging and autologous bone marrow transplantation has become widely acknowledged.

In an effort to develop new anti-neoplastic drugs that would allow selective destruction of leukemic malignant cells, new dye molecules have been prepared and tested as possible new photosensitizers, useful for the photodynamic therapy of leukemias and metastatic cancers. Three new photosensitizers of the pyrylium family were prepared and there is provided evidence for their potential use in the photodynamic treatment of cancers and the leukemias.

The present invention will be more readily understood by referring to the following examples which are given to illustrate the invention rather than to limit its scope.

EXAMPLE I

Method of Treatment of Leukemias

1. Diagnostic procedures

Diagnosis of chronic myelogenous leukemia (CML) will be established using one or more of the following procedures on blood or bone marrow cells:

a) conventional cytogenetics studies with identification of Ph 1+ metaphases harbouring the t(9:22);

b) fluorescent in situ hybridization for the detection of the bcr/abl rearrangement; and c) Southern blot analysis for the detection of a rearranged bcr fragment or PCR-RT for the detection of chimeric bcr/abl messenger RNA.

2. Bone marrow harvesting

After diagnosis, bone marrow (BM) or peripheral blood (PB) derived hemopoietic stem cells will be harvested using previously described procedures for the autologous marrow transplantation in cancer therapy (reviewed by Herzig GP, (1981) *Prog. Hematol.*, 12:1). Hemopoietic stem cells collected for autograft will be immediately treated ex vivo as described below.

3. In vitro purging of leukemia

Ex vivo treatment will consist of short-term incubation or BM of PB stem cells with one or several of the selected photoactive compounds. Duration of incubation, cell concentration and drug molarity will be determined for each patient using an aliquot of the harvested cell population. Excess of dyes will be removed by cell washes with sterile dye free medium supplemented with 2% autologous serum. Cells will next be exposed to radiant energy of sufficient intensities to effect photodynamic purging of leukemia cells. Efficacy of the photodynamic purging procedure will be verified on an aliquot of the treated cell population, before cryopreservation and/or re-infusion to the patient is performed. Until re-infusion to the patient, the cells will be cryopreserved in 10% dimethyl sulfoxyde (DMSO)—90% autologous serum medium, at −196° C. in the vapour phase of liquid nitrogen.

4. Systemic treatment of patients

Following stem cell harvest, patient will be either treated with conventional regimens until autografting is clinically indicated or immediately submitted to dose-intensive chemotherapy and total body irradiation where indicated.

5. Autologous stem cell transplantation

Following appropriate treatment of the patient by high-dose chemotherapy and irradiation and at the appropriate clinical moment, cryopreserved marrow or peripheral blood stem cells will be rapidly thawed and diluted in medium containing 25 UI DNase ml$^{-1}$ to minimize clumping. A minimum of $2 \times 10^7$/kg nucleated cells with 85% to 95% viability as measured by Trypan™ blue exclusion will be returned to the patient.

EXAMPLE II

Method of Treatment of Malignancies

1. Diagnostic procedures

Diagnosis of malignancies will be established using conventional histopathological examination of the primary tumor. Detection of marrow involvement by neoplastic cells will be achieved by direct histological examination and ancillary procedures where indicated (i.e. immuno-peroxydase, immunohistochemical, tumor markers and hybridization studies).

2. Bone marrow harvesting

After diagnosis, bone marrow (BM) or peripheral blood (PB) derived hemopoietic stem cells will be harvested using previously described procedures for the autologous marrow transplantation in cancer therapy (reviewed by Herzig GP, (1981) *Prog. Hematol.*, 12:1). Hemopoietic stem cells collected for autograft will be treated immediately ex vivo as described below.

3. In vitro purging of leukemia

Ex vivo treatment will consist of short-term incubation of BM of PB stem cells with one or several of the selected photoactive compounds. Duration of incubation, cell concentration and drug molarity will be determined for each patient using an aliquot of the harvested cell population. Excess of dyes will be removed by cell washes in sterile dye free medium supplemented with 2% autologous serum. Cells will next be exposed to radiant energy of sufficient intensities to effect photodynamic purging of leukemia cells. Whenever a sensitive molecular marker is available, an aliquot of the treated cell population will be tested for the detection of residual neoplastic cells before cryopreservation and/or re-infusion to the patient is attempted. The cells will be cryopreserved in 10% dimethyl sulfoxyde (DMSO)—90% autologous serum medium, at 196° C. in the vapour phase of liquid nitrogen.

4. Systemic treatment of patients

Following stem cell harvest, patient will be either treated with conventional regimens until autografting is clinically indicated or immediately submitted to dose-intensive chemotherapy and total body irradiation where indicated.

5. Autologous stem cell transplantation

Following high-dose chemotherapy and irradiation cryopreserved marrow or peripheral blood stem cells will be rapidly thawed and diluted in medium containing 25 UI DNase $Ml^{-1}$ to minimize clumping. A minimum of $2\times10^7$/kg nucleated cells with 85% to 95% viability as measured by Trypan™ blue exclusion will be returned to the patient.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A photoactivable rhodamine derivative with high quantum yield of singlet oxygen generation and differential retention between normal and cancer cells, said derivative being selected from the group consisting of 2-(4,5-dibromo-6-amino-3-imino-3H-xanthen-9-yl)-benzoic acid methyl ester hydrochloride and 2-(4,5-dibromo-6-amino-3-imino-3H-xanthen-9-yl)-benzoic acid butyl ester hydrochloride.

* * * * *